(12) United States Patent
Lothert

(10) Patent No.: US 7,467,007 B2
(45) Date of Patent: Dec. 16, 2008

(54) RESPIRATORY GATED IMAGE FUSION OF COMPUTED TOMOGRAPHY 3D IMAGES AND LIVE FLUOROSCOPY IMAGES

(75) Inventor: Mark Lothert, Conroe, TX (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/434,694

(22) Filed: May 16, 2006

(65) Prior Publication Data

US 2007/0270689 A1    Nov. 22, 2007

(51) Int. Cl.
*A61B 5/05* (2006.01)
(52) U.S. Cl. .................................. 600/428
(58) Field of Classification Search ............ 600/407, 600/424, 428; 378/19; 128/899
See application file for complete search history.

(56) References Cited

U.S. PATENT DOCUMENTS

| | | | |
|---|---|---|---|
| 4,838,265 A | 6/1989 | Cosman et al. | |
| 6,272,370 B1 | 8/2001 | Gillies et al. | |
| 6,298,259 B1 | 10/2001 | Kucharczyk et al. | |
| 6,351,513 B1 | 2/2002 | Bani-Hashemi et al. | |
| 6,351,573 B1 | 2/2002 | Schneider | |
| 6,370,417 B1 | 4/2002 | Horbaschek et al. | |
| 6,370,421 B1 | 4/2002 | Williams et al. | |
| 6,389,104 B1 | 5/2002 | Bani-Hashemi et al. | |
| 6,606,513 B2 | 8/2003 | Lardo et al. | |
| 6,628,977 B2 | 9/2003 | Graumann et al. | |
| 6,725,080 B2 | 4/2004 | Melkent et al. | |
| 6,813,512 B2 | 11/2004 | Aldefeld et al. | |
| 6,923,768 B2 | 8/2005 | Camus et al. | |
| 6,937,883 B2 | 8/2005 | Prince | |
| 2002/0085681 A1 | 7/2002 | Jensen | |
| 2003/0114752 A1 | 6/2003 | Henderson et al. | |
| 2003/0128801 A1 | 7/2003 | Eisenberg et al. | |
| 2003/0181809 A1 | 9/2003 | Hall et al. | |
| 2004/0077942 A1 | 4/2004 | Hall et al. | |
| 2004/0081269 A1* | 4/2004 | Pan et al. ................. 378/4 |
| 2004/0097805 A1* | 5/2004 | Verard et al. ............ 600/428 |
| 2005/0020914 A1 | 1/2005 | Amundson et al. | |
| 2005/0053192 A1 | 3/2005 | Sukovic et al. | |
| 2005/0065430 A1 | 3/2005 | Wiethoff et al. | |
| 2005/0096543 A1 | 5/2005 | Jackson et al. | |
| 2005/0137661 A1 | 6/2005 | Sra | |
| 2005/0143777 A1 | 6/2005 | Sra | |
| 2005/0165301 A1 | 7/2005 | Smith et al. | |
| 2005/0171428 A1 | 8/2005 | Fichtinger et al. | |
| 2005/0288578 A1 | 12/2005 | Durlak | |

* cited by examiner

*Primary Examiner*—Eric F Winakur
*Assistant Examiner*—Michael T Rozanski
(74) *Attorney, Agent, or Firm*—Alexander J. Burke; Peter L. Kendall

(57) ABSTRACT

A system and method is provided directed to improved real-time image guidance by uniquely combining the capabilities of two well-known imaging modalities, anatomical 3D data from computer tomography (CT) and real time data from live fluoroscopy images provided by an angiography/fluoroscopy system to ensure a more efficient and safer intervention in treating punctures, drainages and biopsies in the abdominal and thoracic areas of the human body.

4 Claims, 3 Drawing Sheets

US 7,467,007 B2

RESPIRATORY GATED IMAGE FUSION OF COMPUTED TOMOGRAPHY 3D IMAGES AND LIVE FLUOROSCOPY IMAGES

BACKGROUND

1. Field of the Invention

The present invention is generally directed to medical imaging. More particularly, the present invention is directed to an advanced respiratory-gated image fusion system and methods for use in the image-assisted treatment of punctures, drainages and biopsies in the abdominal and thoracic areas of the human body.

2. Background of the Invention

Respiratory motion can introduce significant challenges during non-vascular interventions like RF ablations, biopsies and radiotherapy treatment. The challenges that are introduced during these types of interventions are related to the manner in which they are supported. These types of interventions are presently supported by ultrasound guidance or CT guidance. One drawback of using ultrasound or CT guidance is the lack of real time 3D support. To reconcile this lack of real time 3D support, i.e., the time-varying discrepancy between the navigation positions and the pre-operative image data caused by the heart contraction is the use of time-resolved CT data acquisition (e.g., 4D Computed Tomography) which explicitly includes organ/target motion in treatment planning and delivery. However, a drawback of utilizing time-resolved CT data acquisitions is the amount of space required around the patient, which is restricted by MR or CT gantry design. The open C-arm concept of angiography and catheter laboratory systems overcomes the space restrictions, however, it suffers from a lack of real time 3D/4D capabilities.

As such there is a need for a real-time image guidance system for use in treating punctures, drainages and biopsies in the abdominal and thoracic areas of the human body that overcomes the afore-mentioned and other drawbacks of the prior art.

SUMMARY OF THE INVENTION

The present invention provides new and improved methods and systems for providing real-time image guidance by uniquely combining the capabilities of two well-known imaging modalities, anatomical 3D data from computer tomography (CT) and real time data from live fluoroscopy images provided by an angiography/fluoroscopy system to ensure a more efficient and safer intervention in treating punctures, drainages and biopsies in the abdominal and thoracic areas of the human body.

The system and method of the invention provides a number of advantages over the prior art including, but not limited to, (a) reducing the negative impact of respiratory related organ movements (e.g., liver) during an interventional procedure by combining real time data from fluoroscopy with anatomical 3D data from CT, (b) providing improved accuracy, i.e., needle guidance, during biopsies, punctures and drainages and (c) providing patient access in an open C-arm environment.

BRIEF DESCRIPTION OF THE DRAWINGS

A wide array of potential embodiments can be better understood through the following detailed description and the accompanying drawings in which.

In the drawings, the same or similar elements are denoted by the same reference numerals even though they are depicted in different drawings.

DETAILED DESCRIPTION OF EXEMPLARY EMBODIMENT

As required, detailed embodiments of the present inventions are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1A:
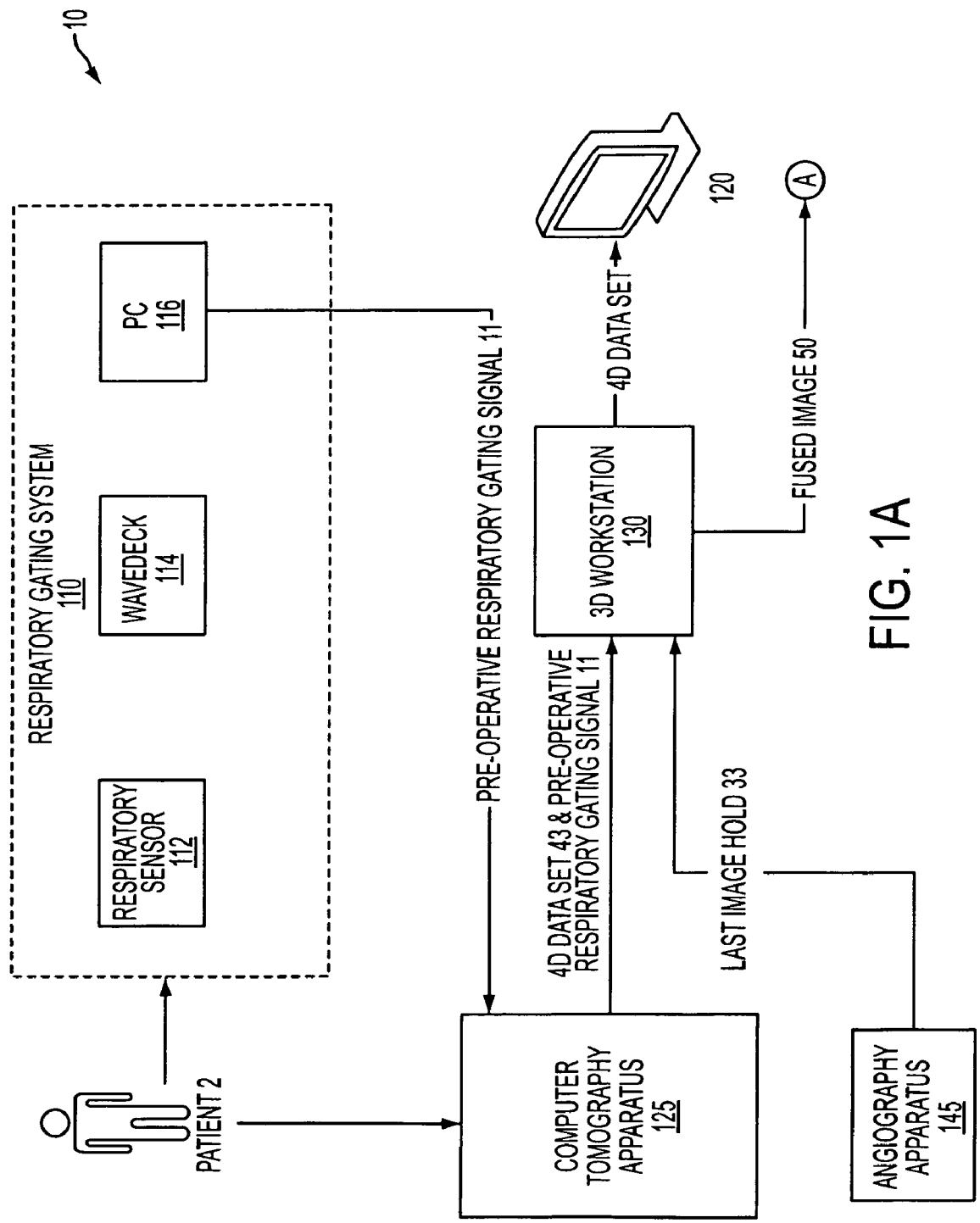
FIGS. 1a & 1b show one embodiment of a system for providing improved image guidance in an interventional medical procedure.
Figure 1B:
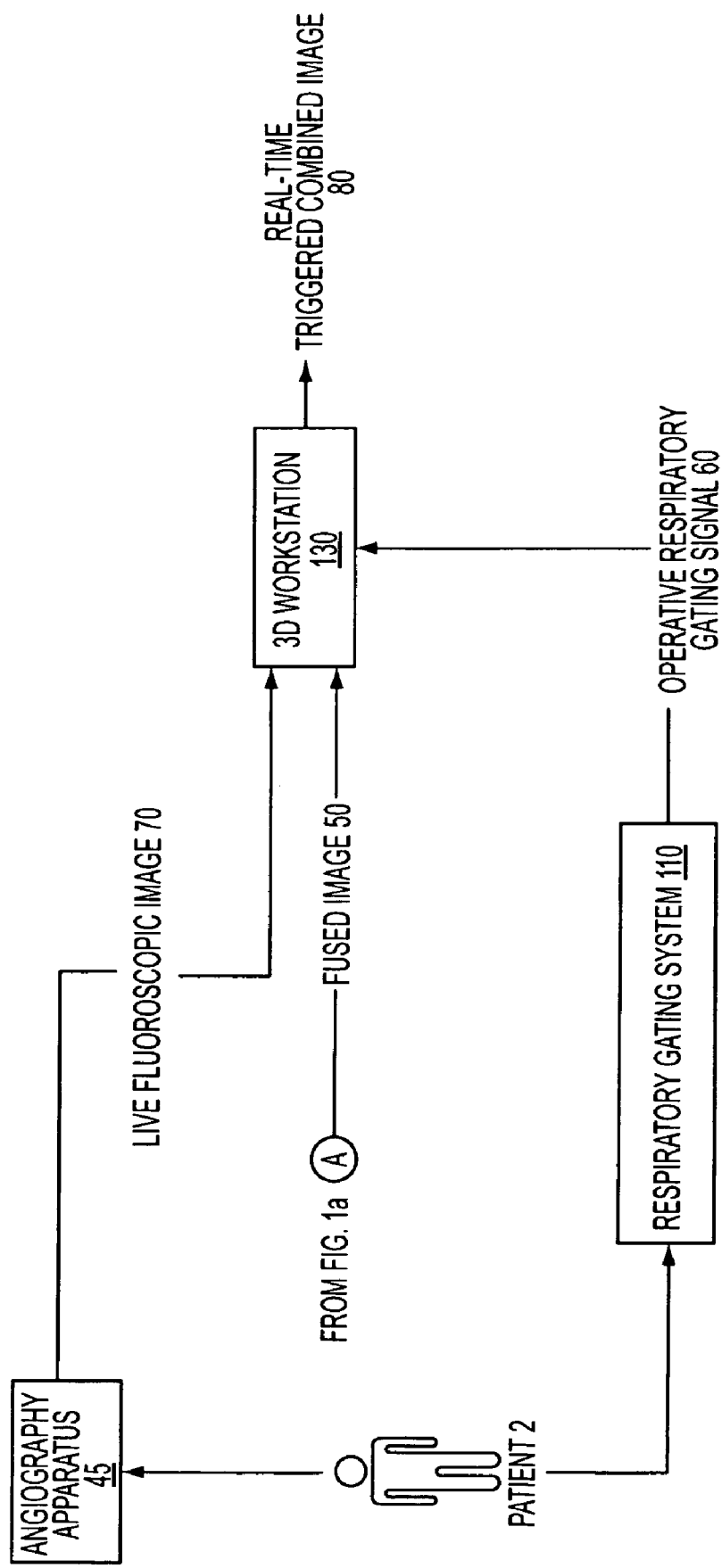

Referring now to FIGS. 1a & 1b, according to an embodiment of the present invention, a system 10 for implementing the present invention can comprise, inter alia, a respiratory gating sub-system 110 comprising a respiratory sensor 112, a wave-deck device 114 and a personal computer (PC) 116. The system 10 can further comprise computer tomography (CT) apparatus 125, a 3D workstation 130, a display 120 and angiography apparatus 145.

System 10 may include less or more elements than depicted in FIGS. 1a and 1b. System 10 may also be packaged in suitable manners other than that shown in FIGS. 1a and 1b. For example, system 10 may be aggregated by an entity that is to deliver an interventional medical procedure, such as a hospital.

The respiratory sensor 112 comprises any sensor capable of detecting the respiratory motion changes of a patient. The sensor is capable of detecting the mechanical expansion of the thoracic cavity resulting from the respiratory motion as the pressure changes in accordance with the up/down movement of the chest and abdomen. The sensor detects the distance change to the chest surface with the expansion of the thoracic cavity resulting from the respiratory motion of the chest and abdomen.

The wave-deck device 114 is a device capable of processing received signals and converting the received signals into a serial format for transmission to the Personal Computer (PC) 116.

The three-dimensional (3D) workstation 130 is a general processor, a data signal processor, graphics card, graphics chip, personal computer, motherboard, memories, buffers, scan converters, filters, interpolators, field programmable gate array, application specific integrated circuit, analog circuits, digital circuits, combinations thereof or any other now known or later developed device for generating three-dimensional or two-dimensional representations from input data in any one or more of various formats. The three-dimensional (3D) workstation 130 includes software or hardware for rendering a three-dimensional representation, such as through alpha blending, minimum intensity projection, maximum intensity projection, surface rendering, or other now known or later developed rendering technique. The three-dimensional (3D) workstation 130 also has software for generating a two dimensional image corresponding to any plane through the volume. The software may allow for a three-dimensional rendering bounded by a plane through the volume or a three-dimensional rendering for a region around the plane.

The display 120 comprises a monitor, CRT, LCD, plasma screen, flat panel, projector or other now known or later developed display device. The display 120 is operable to generate images for a two-dimensional view or a rendered three-dimensional representation. For example, a two-dimensional image representing a three-dimensional volume through rendering is displayed.

The method of the invention can be generally divided into two stages, (1) a pre-operative stage that generates and outputs a landmark or image based fused image 50 (see FIG. 1*a*) and (2) a operative stage (see FIG. 1*b*) in which the landmark or image based fused image is combined with a live fluoroscopic image 70 to be triggered by a respiratory gating signal 60 to generate a real-time triggered combined image 80 that provides improved imaging capabilities for assisting a user in performing a non-vascular interventional procedure.

Figure 2:
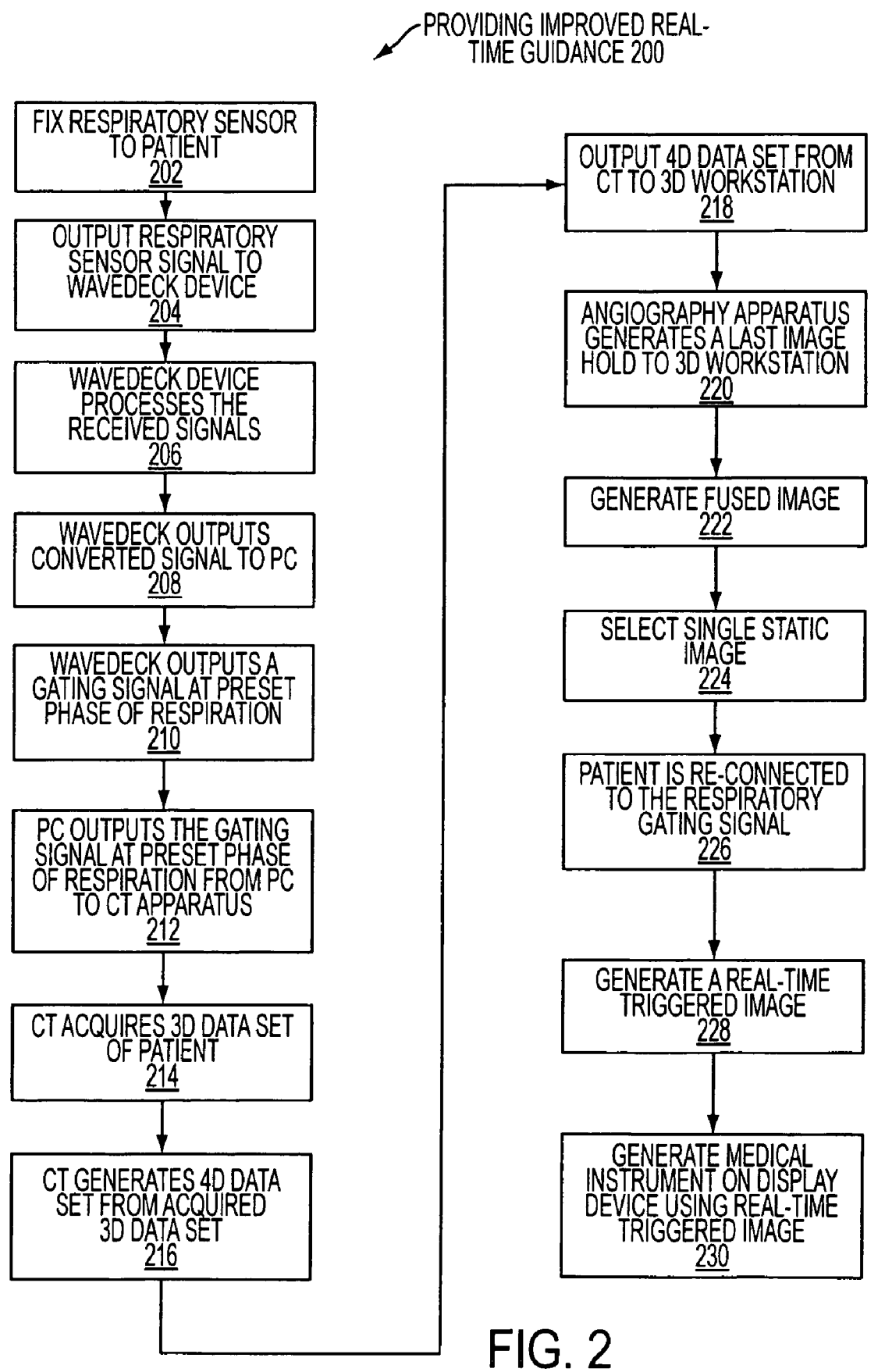
FIG. 2 is a flow chart showing a process for providing real time image guidance in accordance with an embodiment of the present invention.

FIG. 2 is a flow diagram of method steps 200 for providing improved real-time image guidance to perform an interventional procedure, according to one embodiment of the present invention. As stated above, the method uniquely combines the capabilities of anatomical 3D data from computer tomography (CT) and real time data from live fluoroscopy images provided by an angiography/fluoroscopy system to provide improved image guidance.

Method steps 200 may be embodied, in whole or in part, by hardware of and/or software executed by elements including but not limited to those of system 10. Software embodying one or more of process steps 200 may be stored by any medium, including a fixed disk, a floppy disk, a CD-ROM, a DVD-ROM, a Zip.™. disk, a magnetic tape, or a signal. Some or all of such software may also be stored in one or more devices. One or more of process steps 200 may be performed manually.

Initially, at step 202, the respiratory sensor 112 is fixed directly to, or within close proximity, of a patient 2.

At step 204, the signals output from the respiratory sensor 112 are detected and output to the Wave Deck device 114.

At step 206, the Wave Deck device 114 processes the signals received from the respiratory sensor 112 and converts the received signals into a serial format for transmission to the Personal Computer (PC) 116.

At step 208, the Wavedeck device 114 outputs the converted signals to the PC 116.

At step 210, The PC 116 continuously monitors the respiratory signals received from the Wave Deck device 114 and commands the Wave Deck device 114 to output a respiratory gating (TTL) signal 11 when the monitored respiratory signal reaches a preset phase of respiration. A preset phase of respiration, as defined herein, refers to a specific stage during the respiratory cycle. This cycle is reflected in an increase or a decrease especially of the lateral dimensions of the thoracic cavity. In various embodiments, more than one phase may be used to trigger to trigger the 3D data set at step 214. Alternatively, a single phase may be used, such as, for example, selecting a phase corresponding to maximum inspiration or expiration during a physiological respiratory cycle.

At step 212, at the time at which the monitored respiratory signal reaches a preset phase of respiration as described at step 210, the gating (TTL) signal 11 is transmitted from the PC 116 to the CT tomography scanner 20.

At step 214, a computer tomography (CT) apparatus 125 performs a CT based acquisition of a three dimensional (3D) dataset of a patient's region of operative interest. The dataset is obtained by placing the patient 2 in the computed tomography (CT) apparatus 125.

At step 216, the computer tomography (CT) apparatus 125 generates a four dimensional (4D) data set 43 from the 3D data set obtained at step 214. The four dimensional (4D) data set 43, is essentially an animated "movie" of the 3D data set. The time duration of the 4D data corresponds substantially to one respiratory cycle of the 3D data set. In an embodiment, the 4D data set 43 may be generated by over-sampling a CT data acquisition at each slice. During several CT tube rotations, projection data is collected in axial cine mode for the duration of the patient's respiratory cycle, plus the time needed for a full CT gantry rotation. Multiple images are then reconstructed per slice that is evenly distributed over the acquisition time. Each of these images represents a different anatomical state during a respiratory cycle.

At step 218, The 4D data set 43, generated at step 216, is output from the CT apparatus 125 to the 3D workstation 130 along with the respiratory gating signal 11 as a first input to the 3D workstation 130, as shown in FIG. 1*a*.

At step 220, the angiography apparatus 145 generates and outputs a "last image hold (LIH)" 33 of the patient's region of operative interest to the 3D workstation 130 as a second input to the 3D workstation 130, as shown in FIG. 1*a*. The "last image hold" (LIH) 33 is the last image that is displayed after a sequence of fluoroscopy images. This "last image hold" (LIH) 33 is stored on a hard disk (not shown) of the angiography apparatus 145 to be output to the 3D workstation 130.

At step 222, at the 3D workstation 130, upon receiving the first and second inputs described above at respective steps 218 and 220, an image registration and fusion process is applied to generate and output a fused 2D/3D image 50 as a first output of the 3D workstation 130. Generally, Image Fusion allows spatial alignment and visualization of image data of a patient where the image data has been generated at different points in time or by different modalities. It supports optimal diagnosis (fusion of morphological and functional information) and therapy planning. Image fusion generally operates by performing a visual alignment with up to 6 degrees of freedom (i.e., 3× translation, 3× rotation). Then, a landmark registration is performed with point-based registration using anatomical landmarks. Then, a transformation matrix is stored after registration for later retrieval with datasets. The results are displayed on the display of the 3D workstation 130 or on any other display connected to the 3D workstation 130 (i.e. additional location close to angiography apparatus).

As is well known to those in the art, the process of registration, also referred to as image fusion, superimposition, matching or merge, is based on a transformation that transforms an image of one modality to an image of another modality. In other words, image registration attempts to map each point in a first image to a corresponding point in a second (transformed) image. It should be appreciated that while the instant example refers to landmark registration, other registration methods are within contemplation of the invention. Such registration methods include, without limitation, intensity based image fusion which performs an intensity matching using mutual intensity information to co-register different images. The matched intensities may be derived from the same scanner (e.g., two different MRI scans acquired on different days) or from different modalities. Other registration methods contemplated for use with the invention include, control-point based registration, moment-based registration and edge-based registration.

Control-point based registration operates by defining control-points in an image. These points or landmarks are typically selected as features and/or geometric properties that are unique to an image. These points or landmarks can be used extrinsically, intrinsically or as a combination of each. They can be internal anatomic landmarks (rib cage, ventricles, bone surfaces, etc.) or external point sources attached to the patient, or external fiducial markers in stereotactic studies.

Moment-based registration operates by extracting common information from images with or without minimal participation of the user. Gray-level and geometric properties of images are characterized by the center of gravity, principal axis and more complex moments. Parameters (translation, rotation, scaling, etc.) of the transform leading to "standard" images are computed by normalizing moments in each image. The main property of the normalized moments is that they are invariant features of images.

Edge-based registration is typically utilized to register images where neat contours exist. The preprocessing stage consists of discarding all information except edges in each image.

At step 224, an operator reviewing the 4D data set displayed on the display device 120 as a second output of the 3D workstation 130, selects a single static (3D) image from the 4D data set being displayed. The single static (3D) image is selected, in one embodiment, based on a set of anatomical landmarks to be correlated to with corresponding landmarks from the "last image hold" 33. For example, given an exemplary 4D data set (i.e., "animated movie") comprised of 10 static images. An operator may select the $4^{th}$ static image on the basis of it being an optimal image for associating a set of anatomical landmarks (e.g., tip of a spine body or bony structures of the ribcage) viewed in the static image with corresponding landmarks viewed in the "last image hold" 33, i.e., the live fluoroscopic image output from the angiography apparatus 145.

Initially, at the beginning of the operative stage, at step 226, the patient 2 is re-connected to the respiratory gating system 110 to acquire an "operative" respiratory gating signal 60 as distinguished from the "pre-operative" gating signal 11 obtained during the pre-operative stage. However, it is noted that the process of obtaining both the "pre-operative" and "operative" gating signals are identical. The operative respiratory gating signal 60 is provided as a first input to the 3D workstation 130.

At step 228, the 3D workstation 130 generates a real-time triggered combined image 80 by combining the fused image 50, provided as an output of the pre-operative stage with a live fluoroscopic image 70 of the patient 2, obtained during the operative stage and triggering the combined image with the operative respiratory gating signal 60. It is noted that triggering the combined image at the operative stage occurs in a different manner than that discussed above (see steps 210-214) for triggering the 3D data set in the pre-operative stage. The trigger that is applied at step 228 utilizes a phase corresponding to the end of expiration of the smallest thoracic diameter (i.e., the point of the first increase in diameter of the thoracic, which is indicative of the start of expiration).

At step 230, Biopsy needles or ablation instruments may be displayed in real time on a display device using the real-time triggered combined image 80 generated at step 228 to provide improved real-time imaging guidance. It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures are preferably implemented in software, the connections between system modules (or the logic flow of method steps) may differ depending upon the manner in which the present invention is programmed. Given the teachings herein, one of ordinary skill in the related art will be able to contemplate these and similar implementations of the present invention.

The embodiments of the present invention overcomes the challenges presented by respiratory motion which occurs during non-vascular interventions like RF ablations, biopsies and radiotherapy treatment. The invention overcomes these challenges by reducing the negative impact of respiratory related organ movements (e.g., liver) during an interventional procedure by combining real time data from fluoroscopy with anatomical 3D data from CT, which provides improved accuracy, i.e., needle guidance, during biopsies, punctures and drainages and allows for patient access in an open C-arm environment.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for providing real-time image guidance in an image-guided medical procedure, the method comprising:
   (a) constructing, in a pre-operative stage of said procedure, a fused image comprising a single image of a computer tomography (CT) generated anatomical 4D data set of a patient's region of operative interest with a static fluoroscopic image of said patient's region of operative interest;
   (b) acquiring, in an operative stage of said procedure, a live fluoroscopic image of said patient's region of operative interest;
   (c) acquiring, in said operative stage, an operative respiratory gating signal of the patient, substantially coincident with said step (b); and
   (d) triggering, in said operative stage, the fused image, obtained at said step (a), with the live fluoroscopic image, obtained at said step (b) by the real-time respiratory gating signal, obtained at said step (c) to generate a real-time fused, and triggered image of said patient's region of operative interest;
   wherein the fused and triggered image provides real-time image guidance during said image-guided medical procedure by displaying a medical device in real time to ensure a safer and more efficient intervention
   wherein the constructing step (a) further comprises
   acquiring a pre-operative respiratory gating signal of the patient's respiratory movement, at substantially a point in time when the monitored respiratory signal reaches a preset phase of respiration;
   acquiring an anatomical 3D data set of a patient's region of operative interest;
   constructing an anatomical 4D data set from the acquired anatomical 3D data set;
   acquiring a static fluoroscopic image of said patient's region of operative interest;
   selecting a single frame from the anatomical 4D data set as an optimal image; and statically fusing the selected single frame from the anatomical 4D data set with the acquired static fluoroscopic image.

2. The method of claim 1, wherein the fused image comprises one of a landmark based fused image, surface based fused image, intensity based fused image, and point based fused image.

3. The method of claim 1, wherein the operative respiratory gating signal is acquired at substantially a point in time when the monitored respiratory signal reaches a preset phase of respiration.

4. The method of claim 1, wherein the step of identifying a single frame from the anatomical 4D data set as an optimal image further comprises:
   simultaneously displaying the anatomical 4D data set and the static fluoroscopic image on a display device; and
   reviewing each frame of the 4D data set and the static fluoroscopic image to identify said single frame as a frame having the highest degree of correlation with the displayed static fluoroscopic image based on a set of common anatomical landmarks.

* * * * *